US006841132B2

(12) United States Patent
Samsoondar (10) Patent No.: US 6,841,132 B2
(45) Date of Patent: Jan. 11, 2005

(54) SAMPLE TAB (75) Inventor: James Samsoondar, Cambridge (CA)

(73) Assignee: Spectromedical Inc., Cambridge (CA)

( * ) Notice: Subject to any disclaimer, the term of this patent is extended or adjusted under 35 U.S.C. 154(b) by 300 days.

(21) Appl. No.: 10/042,258

(22) Filed: Jan. 11, 2002

(65) Prior Publication Data
US 2002/0110496 A1 Aug. 15, 2002

Related U.S. Application Data (63) Continuation-in-part of application No. 09/958,933, filed as application No. PCT/CA00/00549 on May 11, 2000, now Pat. No. 6,582,964.
(60) Provisional application No. 60/133,876, filed on May 12, 1999.

(30) Foreign Application Priority Data

May 11, 2000 (CA) .............................. PCT/CA00/00549

(51) Int. Cl.[7] ................................................. B01L 3/00
(52) U.S. Cl. .................... 422/102; 422/99; 422/939; 436/164; 436/165
(58) Field of Search ....................... 422/82.05, 82.09, 422/99, 102, 104, 939, 940; 436/164, 165; 435/288.3, 288.7; 600/573

(56) References Cited

U.S. PATENT DOCUMENTS

| 3,876,377 A | * | 4/1975 | Cinqualbre | 422/58 |
|---|---|---|---|---|
| 4,134,678 A | | 1/1979 | Brown et al. | 356/39 |
| 4,387,972 A | * | 6/1983 | Valencia | 359/398 |
| 4,535,778 A | * | 8/1985 | Kitrilakis et al. | 600/349 |
| 4,575,240 A | | 3/1986 | Hess et al. | 356/246 |
| 4,722,598 A | | 2/1988 | Ford | 350/536 |
| 4,734,260 A | | 3/1988 | Lautenschläger | 422/58 |
| 4,791,938 A | * | 12/1988 | Van Valkenburg | 600/576 |
| 5,004,584 A | * | 4/1991 | Rayman | 422/58 |
| 5,207,984 A | * | 5/1993 | Kheiri | 422/58 |
| 5,306,623 A | * | 4/1994 | Kiser et al. | 435/14 |
| 5,430,542 A | | 7/1995 | Shepherd | 350/246 |
| 5,675,410 A | * | 10/1997 | Kanda | 356/244 |
| 5,725,774 A | * | 3/1998 | Neyer | 210/645 |
| 5,800,781 A | * | 9/1998 | Gavin et al. | 422/73 |
| 5,812,312 A | | 9/1998 | Lorincz | 359/397 |
| 5,846,492 A | | 12/1998 | Jacobs et al. | 422/67 |
| 6,268,910 B1 | | 7/2001 | Samsoondar et al. | 356/39 |
| 6,567,214 B2 | | 5/2003 | Lorincz | 359/397 |

FOREIGN PATENT DOCUMENTS

| EP | 376135 | * 7/1990 |
|---|---|---|
| WO | WO 98/39634 | 9/1998 |

* cited by examiner

Primary Examiner—Maureen M. Wallenhorst
(74) Attorney, Agent, or Firm—Katten Muchin Zavis Rosenman (57) ABSTRACT A sample lab for retaining a sample during spectrophorometric analysis includes a base plate, a sample well, and a cover plate. The sample tab may also include one, or more than one overflow opening for draining excess sample, and an overflow channel to retain the excess sample.

29 Claims, 5 Drawing Sheets

SAMPLE TAB

This application is a Continuation-in-Part of U.S. patent application Ser. No. 09/958,933, filed on Jan 23, 2002 now U.S. Pat. No. 6,582,964, issued on Jun. 24, 2003, which is a National Stage Entry of PCT Application No. PCT/CA00/00549, filed on May 11, 2000, which claims priority to U.S. Provisional Application Ser. No. 60/133,876, filed on May 12, 1999.

The invention relates to a tab for retaining a sample for analysis. More particularly, the present invention provides an apparatus and method for sample analysis using a variety of instruments including spectrophotometric or microscopic analysis.

BACKGROUND OF THE INVENTION

Rapid methods for analysis of a compound or a substance of interest within a biological or non-biological sample are desired within the art.

For example, U.S. Pat. No. 4,575,240, U.S. Pat, No. 4,134,678 and U.S. Pat. No. 4,734,260 disclose sample chambers for fluid analysis within automated analysers. In U.S. Pat. No. 4,575,240, the sample chamber is complex comprising input and output ports for adding a fluid sample into a reservoir formed within a prism that is sealed against a window through which light passes through. A spring attached to a door of the chamber is provided so that when the door is closed, the spring urges the prism against a sealing member. U.S. Pat. No. 4,134,678 discloses an, on-line cuvette that can be use within an automated analyser comprising sample input and output ports.

U.S. Pat. No. 4,734,260 discloses a cuvette for liquid sample analysis comprising a thin sample chamber delimited by radiation transmitting members. The chamber is made from a plurality of component parts that when assembled form the cuvette. Ports extend into, and out of, the sample chamber for sample injection and withdrawal. The ports pass through a housing and one of the radiation transmitting members. Plugs are provided to seal the ports after a sample has been introduced into the cuvette.

U.S. Pat. No. 5,430,542 discloses a simplified disposable cuvette made of two transparent plastic cover sheets that are adhesively attached to a third thicker plastic sheet comprising a sample cavity. The disposable cuvette comprises input and output ports, with the input port adapted to be attached to a syringe for sample introduction. Again, only fluid samples may be analysed using this disposable cuvette.

There is a need for a sample chamber that is easy to use and adaptable for a range of applications, including the analysis, of semi-solid and fluid samples. It is an object of the present invention to overcome disadvantages of the prior art.

The above object is met by a combination of the features of the main claims. The sub claims disclose further advantageous embodiments of the invention.

SUMMARY OF THE INVENTION

The present invention relates to a sample tab for retaining a sample for analysis.

The present invention provides a sample tab comprising, a base plate having a top surface and a bottom surface, at least a portion of the base plate adapted to permit transmission of electromagnetic radiation therethrough, a well disposed on the top surface of the base plate for retaining a sample, the well defined by a closed wall extending above the top surface of the base plate, and a cover plate, hingedly attached to the base plate, and moveable between an open and a closed position, wherein at least a portion of the cover plate permits transmission of electromagnetic radiation therethrough, so that when the cover plate is in the closed position an optical path is formed through the portion of the base plate that permits transmission of electromagnetic radiation, the well, and the portion of the cover plate that permits transmission of electromagnetic radiation. Another embodiment of the invention permits the electromagnetic radiation to be reflected off the opposite side of the sample tab, thereby doubling the direct pathlength.

The present invention also provides for a sample tab as described above wherein the closed wall comprises one or more overflow openings, the closed wall surrounded by a containment wall defining an overflow ring therebetween.

The cover plate may be attached to the base plate or may be separate. Further, the sample tab may comprise a locking member that associates with to a corresponding mating member, thereby permitting the cover plate to be attached to the base plate. The locking member may comprise, but is not limited to, a circular ring capable of frictionally engaging an outer portion of a containment wall or one or more clips capable of frictionally engaging and attaching the cover plate to the base plate. The locking members may be located on the base plate, cover plate or both the base plate, and the cover plate. Similarly, the associated mating member that receives the locking member may be located on the base plate, cover plate or both the base plate, and the cover plate.

Also provided by the present invention, there is provided a sample tab as defined above wherein the wall is surrounded by a containment wall defining an overflow ring therebetween. The containment wall may comprise a sealing member on its upper surface. The sealing member may be an O ring, or a pliable material integral with the containment wall.

In a preferred embodiment of the present invention the sample well contains one or more openings or grooves and an overflow ring for collecting excess sample as it is squeezed out by the closing cover plate. Preferably, the cover plate is attached to the tab so that the sample proximate the cover plate hinge makes contact with the cover plate first, and as the cover plate closes, excess sample is squeezed out through the two grooves and into the overflow ring.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 3 depicts various aspects of an embodiment of a sample tab of the present invention.

FIG. 4 depicts various aspects of an alternate embodiment of a sample tab of the present invention.

FIG. 5 depicts various aspects of an alternate embodiment of a sample tab of the present invention.

DESCRIPTION OF PREFERRED EMBODIMENT

The invention relates to a tab for retaining a sample for analysis. More particularly, the present invention provides a sample tab and a method for sample analysis using a variety of instruments including a spectrophotometer or a microscope.

The following description is of a preferred embodiment by way of example only and without limitation to the combination of features necessary for carrying the invention into effect.

The present invention provides a sample tab that may be used for the determination of a substance within a sample using spectrophotometric or microscopic analysis. The sample tab comprising a base plate, a well disposed on the base plate and a cover plate. In a broad aspect, the present invention also provides an apparatus for determining the concentration of a substance in a sample where the apparatus comprises a sample housing for receiving a sample tab; a radiation source; and radiation detector, operatively coupled with a system for providing a determination of the substance within the sample based on the determination of transmitted or reflected radiation.

According to one embodiment of the present invention, the sample housing comprises a block with a slit for inserting the sample tab. The sample tab consists of a base plate with a well on the base plate for containing the sample and a cover plate which can be placed over the well prior to inserting the sample tab in the housing, preferably the cover plate closes automatically when inserted in the sample housing. The well may be of any desired shape and of any suitable volume.

The present invention also provides a method of determining the concentration of a substance within a sample using a sample tab.

For example, which is not to be considered limiting in any manner, the sample tab as described herein may be used to determine the occurrence or concentration of any substance within a biological or non-biological sample. Preferably the sample is a fluid sample, for example but not limited to blood, or a semi-solid sample. A non-limiting example is provided herein where the sample tab of the present invention may be used, in combination with a spectrophotometer, to test a diabetic patient's compliance with their insulin dosing regime by quantifying The amount of $HbA_{1c}$ and Hb contained in a blood specimen taken from the patient, without further treatment of the specimen, and comparing the concentration of $HbA_{1c}$ and Hb within the sample. In this non-limiting example, an elevated ratio of $HbA_{1c}$ reflects a lack of patient compliance. However, it is to be understood that the sample tab of the present invention may be used to determine the concentration of any substance within a sample using spectrophotometric, microscopic, or other analysis that requires that a sample be retained within a translucent or transparent tab. Furthermore, the sample tab as described herein may comprise at least one surface that reflects incident radiation. Examples of other biological samples that may be determined include, but are not limited to whole blood, plasma, serum, sinovial fluid, cerebral spinal fluid. urine, lymph, mucus, faeces, and semen. However, non-biological samples may also be readily tested as described herein. Examples of non-biological samples include, but are not limited to dairy products, for example, milk, cheese, cottage cheese, yoghurt, or ice cream, or beverages, or semi-solid foods. Non-limiting examples of substances that may detected in these samples include Hemoglobin, one or more proteins, albumin, globulin, fat, lactose etc. An example of a non-limiting measurement that can be made is hematocrit in blood.

According to the present invention, there is provided a method of quantification of one or more substances within a sample comprises the steps of:

i) generating a calibration algorithm for each of the substances to be determined;

ii) obtaining a sample and placing the sample into a sample tab;

iii) measuring with a spectrophotometer, absorbance of radiation by each of the substances in the sample; and iv) incorporating the absorbance measured in step (iii) in the algorithms generated in (i), and calculating the concentration of the substances in the sample.

For example which is not to be considered limiting, if the sample is blood, then the concentration of $HaA_{1c}$, and Hb may be determined. In this case the method of quantification of the one or more chemical compounds comprises the steps of;

i) generating a calibration algorithm for catch of the $HbA_{1c}$ and Hb;

ii) obtaining a blood sample and placing the blood sample into a sample tab, iii) measuring with the spectrophotometer, absorbance of radiation by each of the $HbA_{1c}$, and Hb in the blood sample; and iv) incorporating the absorbance measured in step (iii) in the algorithms generated in (i), and calculating the concentration of the $HbA_{1c}$ and Hb in the sample.

Alternatively, one algorithm can be developed for the ratio of $HbA_{1c}$, to Hb expressed as % $HBA_{1c}$.

According to a method of the present invention quantification includes calculation of the first derivatives of at least two portions of a spectrum generated from a scan for each of the chemical compounds being determined, for example but not limited to, $HbA_{1c}$, and Hb which may then be used to calculate each of the $HbA_{1c}$ and Hb concentrations in the sample. Similarly, PLS (Partial Least Squares) or PCA (Principal Components Analysis) may be used depending on the analyte being analysed.

According to another aspect of the present invention, the method as described herein can be used with reflectance instead of absorbance. In the case of reflectance, either the base plate or the cover plate may have a reflective surface or may be made of reflective material. Such a reflective surface or material could include any suitable reflective coating, for example, but not limited to, a ceramic coating, barium sulfate, Spectralon™, SpecTraflect™, or Duraflect™.

Figure 1:
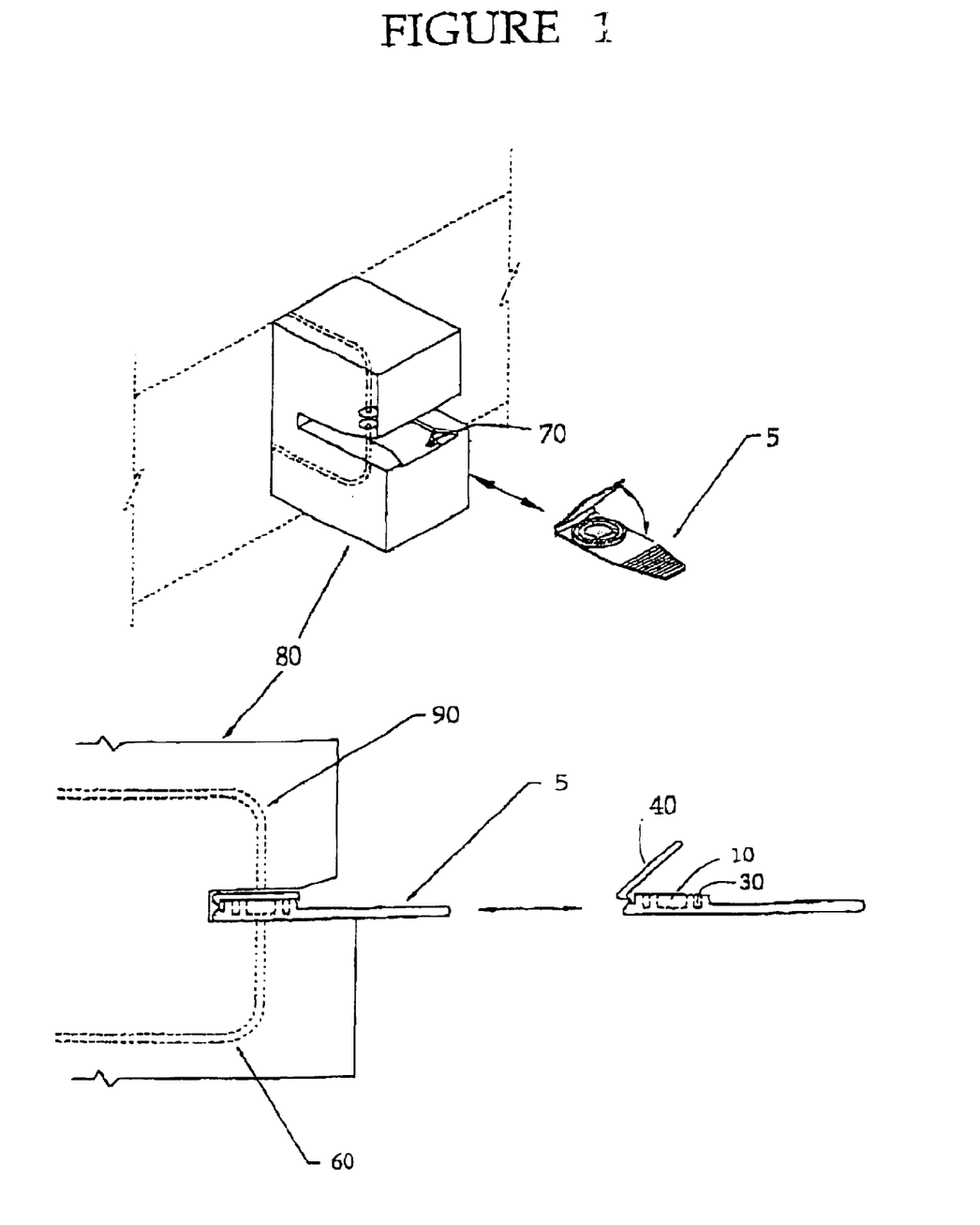
FIG. 1 is a perspective view of a system incorporating an apparatus of the present invention for measuring Hemoglobin Ale.

Turning now to the sample housing within a spectrophotometer and sample tab, as may be seen in FIG. 1, electromagnetic radiation from the spectrophotometer is delivered to the sample in the sample tab (5) through a source or incident optical fibre (60) while the sample rests in a sample tab holder (70) within a sample housing (80). The electromagnetic radiation passing through the sample tab and specimen is received by a receiving optical fiber (90), and processed further to determine concentrations of one or more substances within the sample.

The instrument shown in FIG. 1 is configured for the use of a horizontal sample tab, however the sample tab may also be used in a vertical position within a spectrophotometer or other apparatus. For example, the sample tab may be inserted within a cuvette holder for use within standard spectrophotometers. In this application, the cuvette holder would be configured to hold the sample tab within the path of the radiation beam, as would be the case with a standard cuvette. The cuvette holder can be configured for horizontal or vertical use. However, there are several advantages that may be associated with horizontal use. For example, in sample comprising particulate matter, by maintaining the sample tab horizontally there is a uniform settling of components within the sample, in the direction of the incident radiation beam, such that the particulate matter remains in the light path even after it has travelled. An example of particulate matter is red blood cells in a blood sample.

Sample Tab

According to an aspect of the present invention, there is provided a sample tab for retaining a sample for further analysis, for example, but not limited to using a spectrophotometer or a microscope. A non-limiting example for the use of the sample tab of the present invention is to monitor a diabetic patient's compliance with their insulin dosing regime by spectrophotometry.

The sample tab (5) comprises, a) a base plate (45) with a top surface and bottom surface, the base plate characterized as having at least a portion that permits transmission or reflectance of electromagnetic radiation;

b) a well or sample cavity (10) disposed on the top surface of the base plate for retaining the sample, the well is defined by a closed wall (15) extending above the top surface of the base plate. The well may be of any desired volume and may be of any shape;

c) at least one overflow groove or opening in the wall (20) of the well permitting drainage of excess sample from within the wall;

d) a cover plate (40) having at least a portion that permits transmission or reflectance of electromagnetic radiation.

In use, a sample is retained in the well between the base plate and the cover plate so that electromagnetic radiation may pass through the base plate, through a sample in the well, and the cover plate. However, it is within the scope of the present invention that the radiation beam may travel though the sample, and be reflected off either the base plate or cover plate thereby doubling the path length of the radiation beam. By doubling the path length, a reduced volume of sample may be used during analysis. Either the base plate or the cover plate may have a reflective surface, or may be made of, reflective material.

The sample well defined by a closed wall contains one or more openings or grooves and an overflow ring for collecting excess sample as it is squeezed out by the closing cover plate. Preferably, the cover plate is attached to the tab so that the sample proximate the cover plate hinge makes contact with the cover plate first and as the cover plate closes, excess sample is squeezed out through the grooves, which are preferably situated at the side where the cover plate makes final contact with the rest of the tab, and into the overflow ring. The hinged design helps the sample tab slide into the receptor of an instrument, such as a spectrophotometer.

Figure 2:
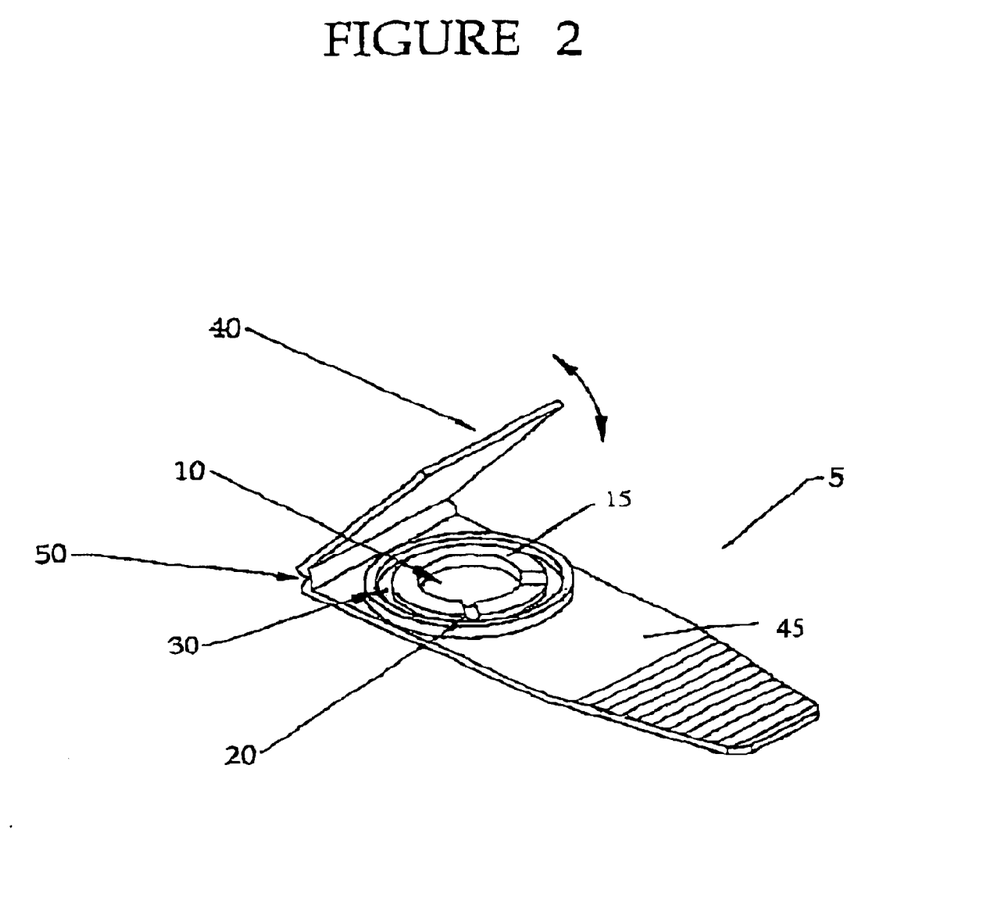
FIG. 2 is a perspective view illustrating the sample tab of the apparatus of FIG. 1.

Referring now to FIG. 2, there is shown an aspect of an embodiment of the sample tab of the present invention. Shown in FIG. 2, is sample tab (5) comprising base plate (45), cover plate (40) and sample well (10) defined by closed wall (15). Sample well (10) may be of any volume required, for example, but not limited to, a size sufficient to allow a drop of blood to fill the well, preferably with some excess. The sample well may also be large enough to accommodate about 10 mL of a sample, for example urine or a beverage. It must be understood that these are just non-limiting examples of sample sizes. In an embodiment which is not meant to be considered limiting in any manner, the well is circular and comprises dimensions of about 4 mm in diameter and about 2 mm in depth. Overflow openings or grooves (20) in closed wall (15) allow excess sample to flow out of sample well (10) when cover plate (40) is closed over sample well (10) and base plate (45). A second wall, such as, but not limited to, a containment wall (37) may be employed to retain the sample that overflows sample well (10), into an overflow ring (30) to prevent leakage of fluid from the sample tab, while permitting a sample of sufficient volume to fill the well. In this regard, the vertical height of containment wall (37) is less than or equal to the height of closed wall (15) defining sample well (10), more preferably it is equal to the height of closed wall (15) defining sample well (10). Cover plate (40) is preferably attached to base plate (45) by hinge (50) or other suitable attachment means known in the art. However, a non-hinged cover plate may also be used. The cover plate may be snapped on to the base plate as described below.

The sample tab may be manufactured from any suitable material known in the art for example, but not limited to, a transparent, translucent material, such as glass, plastic or a combination thereof, or a reflective material. If the base plate and cover plate are transparent or translucent, then it is preferred that the base plate, and cover plate comprise a transparent or translucent plastic, such as but not limited to polypropylene, polycarbonate, polyethylene, or polystyrene, however, a glass plate may also be used. If either of the base plate or cover plate is reflective, then a reflective material, for example but not limited to a ceramic coating, barium sulfate, Spectralon™, Spectraflect™, or Duraflect™ may be used for one of the base or cover plates.

Optionally, the sample tab of the present invention may comprise a locking member to lock cover plate (40) to the base plate (45). The locking member may comprise a portion of the cover plate, base plate or both. Further, the locking member may reversibly or irreversibly lock the cover to the base plate. Any locking member known in the art may be employed with the sample tab of the present invention, for example, but not limited to those as shown in FIGS. 3–5. The use of a containment wall ensures that the sample is retained within the sample tab and reduces contamination between samples. Furthermore, by locking the cover plate of the sample tab in a closed position, the sample tab may be readily disposed of after use without sample leakage, or the sample tab may be used in a vertical position, for example within a cuvette holder adapted for use within spectrophotometers.

Figure 3A:
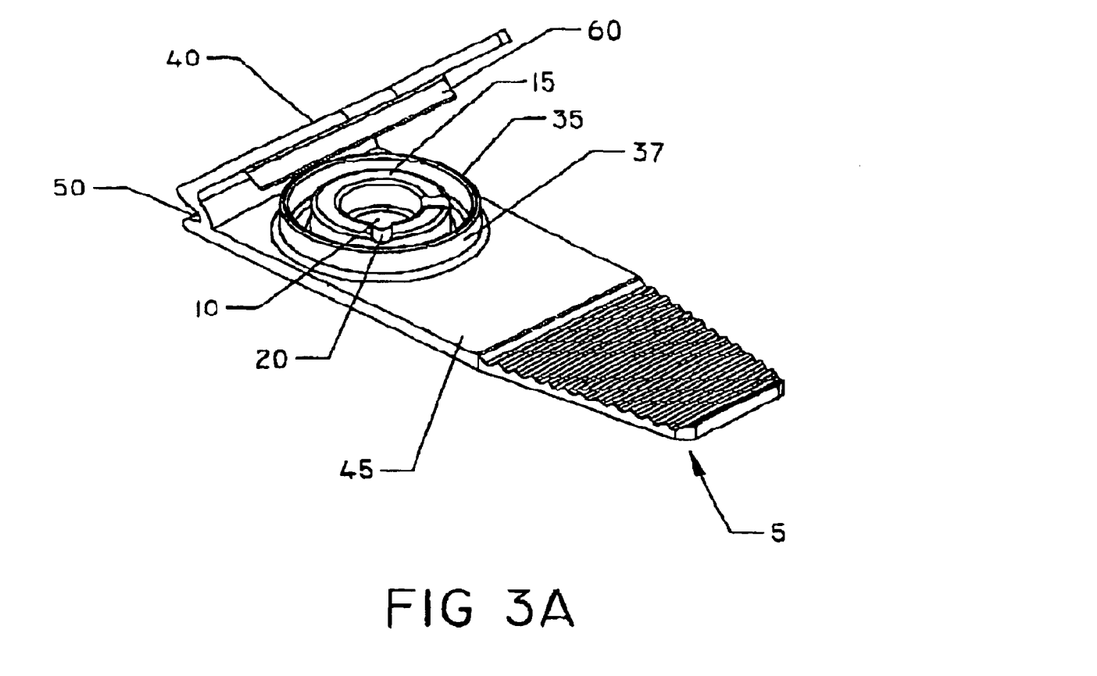
FIG. 3A illustrates an oblique view of the sample tab.
Figure 3B:
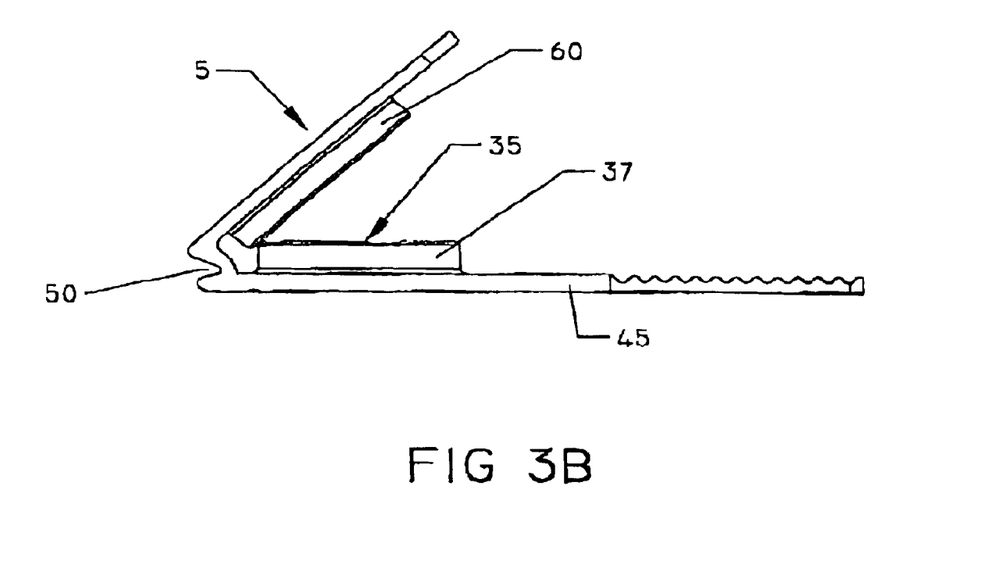
FIG. 3B exhibits a side view of the sample tab.

Referring now to FIG. 3, there is shown an alternate aspect of an embodiment of the present invention. In FIG. 3A, there is shown a perspective view of a sample tab (5) with cover plate (40) positioned over base plate (45) and revealing a well (10) defined by closed wall (15), overflow grooves (20), overflow-ring (30; FIGS. 1 and 2), and hinge (50). FIG. 3B shows a side view of a sample tab (5) wherein cover plate (40) is open. Also shown in FIG. 3B is a locking member (60) which permits cover plate (40) to be fastened to base plate (45). In the aspect of the embodiment shown in FIG. 3B, the locking member (60) comprises a circular ring, capable of frictionally engaging containment wall (37), thereby reversibly attaching cover plate (40) to base plate (45), preventing the escape of a sample from the sample tab. However, as would be evident to someone of skill in the art, the locking member (60) comprising a circular ring may be attached to the base plate (45) in a variety of ways, for example, but not limited to, frictionally engaging a protrusion located on the outside of containment wall (37), or frictionally engaging a recessed groove in the base plate (not shown), adjacent to and below containment wall (37).

When the cover plate is closed over the well, and attached to the base plate, it is preferred that the top surface (35) of the containment wall (37) seals against the lower surface of the cover slip. However, the locking member (60) may also be used to help seal the sample within the sample tab should any leakage occur past the containment wall (37). The embodiment shown in FIG. 3 shows a hinged cover plate, however, it is to be understood that cover plate (40) comprising locking member (60) may be separate from base plate (45), and the cover plate may be attached to the base plate after a sample is introduced into well (10). Since the cover plate is attached to the base plate, the final sample tab assembly serves as one unit.

If it is required that the sample be effectively sealed within well (10), then the upper surface of containment wall (37) may be modified to comprise a sealing member (35), for example an "O ring" that fits within a grooved upper surface of the containment wall, the top surface of the containment wall (37) may be made of a softer pliable material, for example silicon, yet integral with the base plate. Alternatively, the top surface (35) of the containment wall (37) may be lubricated so that when cover slip (40) is attached to base plate (45) a seal is formed between base plate (45) and cover slip (40). The use of a containment wall ensures that the sample is retained within the sample tab and reduces contamination between samples. Furthermore, by locking the cover plate of the sample tab in a closed position, the sample tab may be readily disposed of after use without sample leakage.

Figure 4A:
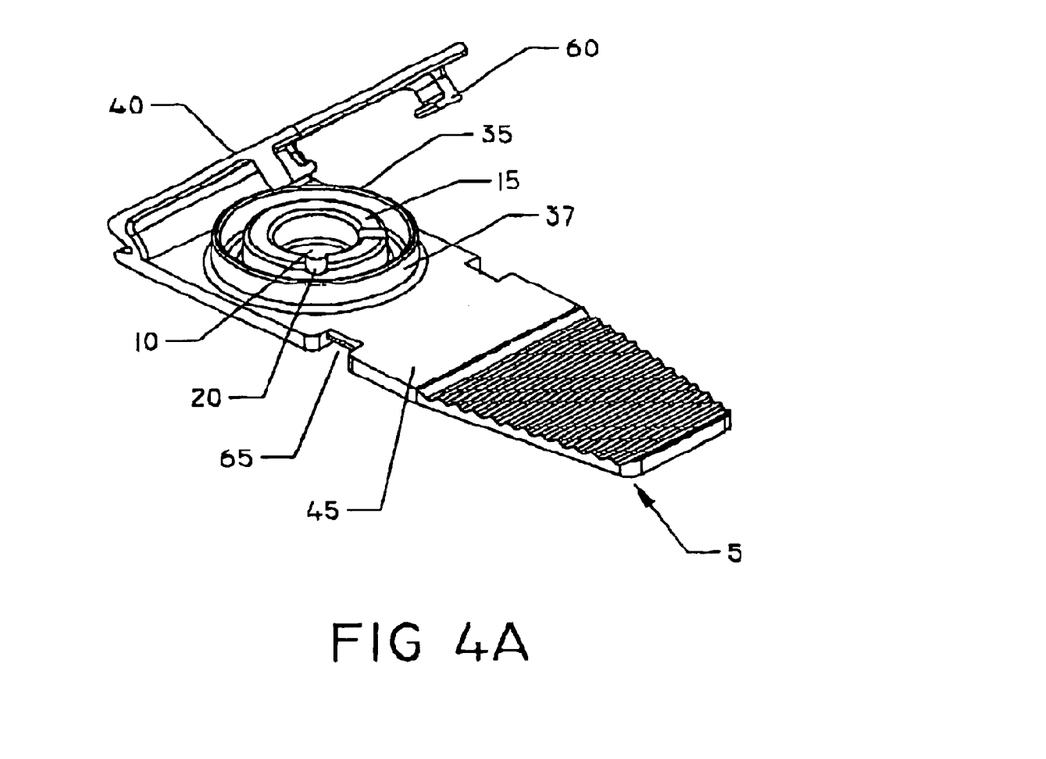
FIG. 4A illustrates an oblique view of the sample tab.
Figure 4B:
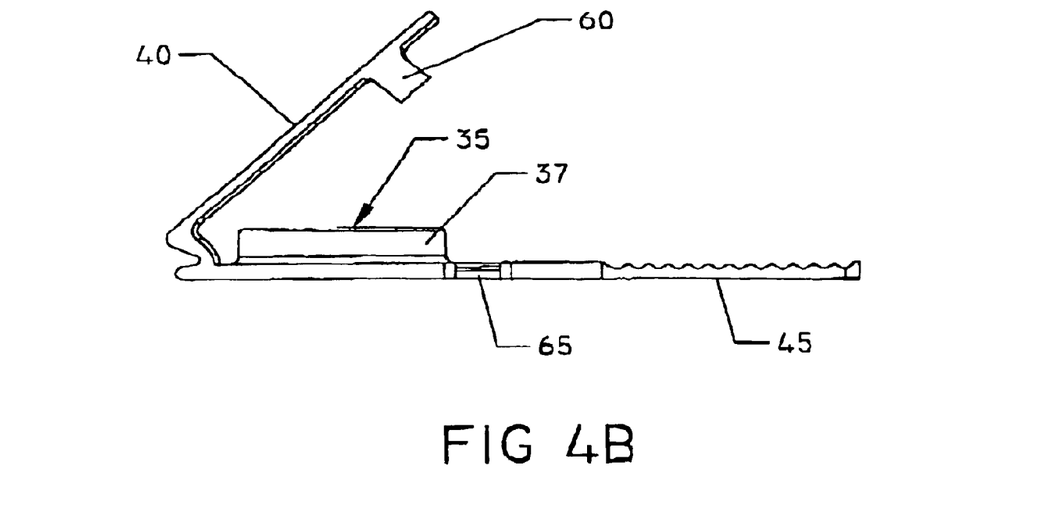
FIG. 4B exhibits a side view of the sample tab.

Referring now to FIG. 4, there is shown an alternate aspect of an embodiment of the present invention. FIG. 4A shows a perspective view, and in FIG. 4B, a side view, of a sample tab (5) with cover plate (40) and base plate (45). In these figures, cover plate (40) is open revealing well (10) defined by closed wall (15), overflow grooves (20), and containment wall (37). Also shown in FIG. 4B are locking members (60) which permit cover plate (40) to be attached to base plate (45). In the aspect of the embodiment shown in FIGS. 4A and 4B, locking members (60) comprise one or more clips capable of frictionally engaging base plate (45), at a corresponding recess (65) within the base plate, thereby locking cover plate (40) to base plate (45) and preventing the escape of a sample from well (10). Locking members (60) may be positioned so that when engaged with the base plate at the corresponding recess (65), they do not extend below the lower surface of the base plate, so that a smooth bottom surface is obtained. Such a smooth surface may be required for sliding the sample tab into a receptor of an apparatus, or for microscopic viewing.

If it is required that the sample be effectively sealed within well (10), then the upper surface of containment wall (37) may be modified to comprise a sealing member (35), for example an "O ring" that fits within a grooved upper surface of the containment wall, the top surface of the containment wall (37) may be made of a softer pliable material, for example silicon, yet integral with the base plate. Alternatively, the top surface (35) of the containment wall (37) may be lubricated so that when cover slip (40) is attached to base plate (45) a seal is formed between base plate (45) and cover slip (40). As described above, the use of a containment wall and optionally a locking cover plate ensures that sample leakage is kept to a minimum.

Figure 5A:
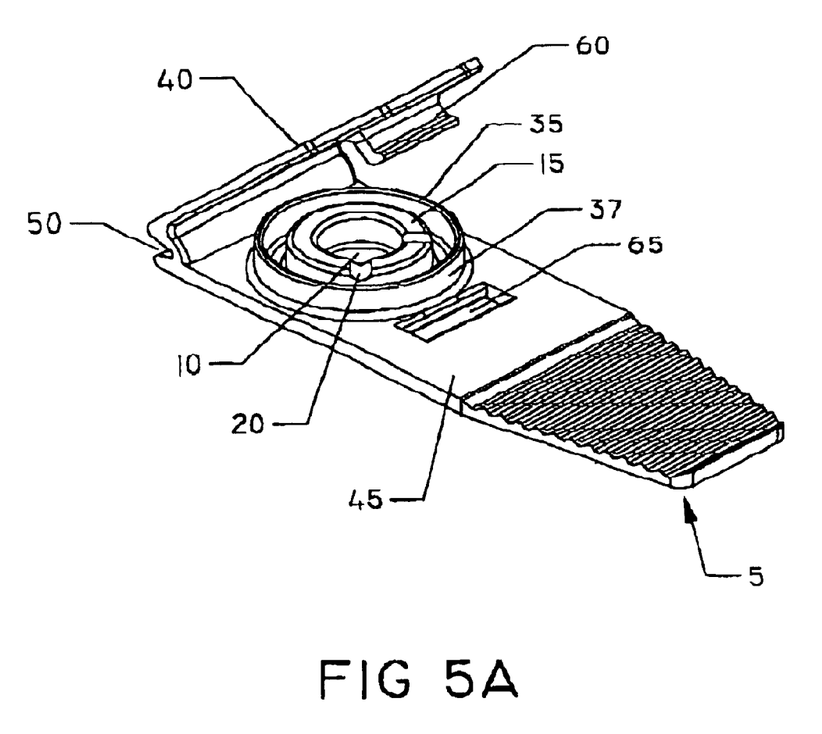
FIG. 5A illustrates an oblique view of the sample tab.
Figure 5B:
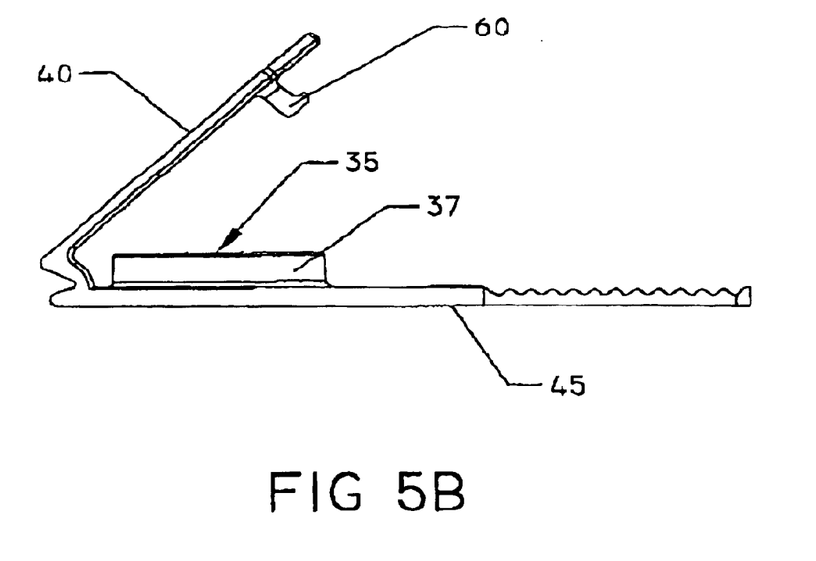
FIG. 5B exhibits a side view of the sample tab.

Referring now to FIG. 5, there is shown another aspect of embodiment of the present invention. In FIG. 5A, there is shown a perspective view, and in FIG. 5B a side view, of sample tab (5) with cover plate (40) positioned over base plate (45). In FIG. 5A, cover plate (40) is open revealing well (10) defined by closed wall (15), overflow grooves (20), containment wall (37) and hinge (50). Also shown in FIG. 5B is locking member (60) which permits cover plate (40) to be attached to base plate (45) by association with a corresponding mating recess (65) positioned on the base plate. In the aspect of the embodiment shown in FIGS. 5A and 5B, locking member (60) comprises a clip capable of frictionally engaging mating recess (65) and locking cover plate (40) to base plate (45), preventing the escape of the sample. The mating recess may extend through the base plate (45), and engage the bottom surface of the base plate, or the locking member may engage a snap portion within recess (65) and not extend thorough the base plate. A smooth bottom surface may be required for sliding the sample tab into a receptor of an apparatus, or for microscopic viewing. It is to be understood that the locking member (60) may be petitioned in the base plate, and recess (65) positioned on the cover slip if desired.

If it is required that the sample be effectively sealed within well (10), then the upper surface of containment wall (37) may be modified to comprise a sealing member (35) so that when cover slip (40) is attached to base plate (45) a seal is formed between base plate (45) and cover slip (40). In this embodiment, the use of a containment wall ensures that the sample is retained within the sample tab and reduces contamination between samples. Furthermore, by locking the cover plate of the sample tab in a closed position, the sample tab may be readily disposed of after use without sample leakage, or it may be used in a vertical position as required.

FIGS. 3–5 illustrate a locking member (60) on the cover plate (40) of the sample tab (5) of the present invention. However, it is also possible that locking member (60) may comprise a portion of base plate (45), and that the corresponding recess (65) be positioned on the cover plate (40).

The sample tab of the present invention may retain any sample for analysis using any suitable instrument, for example, but not limited to spectroscopic or microscopic analysis. Preferably the sample tab retains a fluid or semi-solid sample, for example, but not limited to non-biological, or biological samples. Examples of non-biological samples include, but are not limited to dairy products, for example, milk, cheese, cottage cheese, yoghurt, or ice cream, or beverages, or semi-solid foods. Examples of biological fluids include, but are not limited to whole blood, plasma, serum, sinovial fluid, cerebral spinal fluid, urine, lymph, mucus, faeces, and semen.

The embodiments shown in FIGS. 2–5 are meant to be exemplary rather than limiting in any manner. Those of skill in the art will understand that modifications of the sample tab, base plate, cover plate and locking member, or a combination thereof may be made without departing from the spirit and scope of the present invention, and it is fully intended that such modifications are contemplated by the sample tab of the present invention.

The sample tab as described herein may be used within a spectrophotometer using standard methods as known in the art, for example as disclosed in U.S. Pat. Nos. 5,846,492, 6,268,910, WO 98/39634 (all of which are incorporated herein by reference). These references disclose the spectrophotometric analysis of a biological fluid within a plastic or polyethylene container, for example blood bag tubing (U.S. Pat. No. 6,268,910), or a pipette tip (WO 98/39634; U.S. Pat. No. 5,846,492) However, it is to be understood that the sample tab as described herein may be readily adapted for other analytical uses including microscopic analysis.

The above description is not intended to limit the claimed invention in any manner. Furthermore, the discussed combination of features might not be absolutely necessary for the inventive solution.

All references are herein incorporated by reference.

The present invention has been described with regard to preferred embodiments. However, it will be obvious to persons skilled in the art that a number of variation and modifications can be made without departing from the scope of the invention as described herein.

The embodiment of the invention in which an exclusive property of privilege is claimed are defined as follows:

1. A sample tab comprising:
   a base plate having a top surface and a bottom surface;
   a well defined by a top surface of a section of said base plate and by a wall extending above said top surface of said base plate, and
   a cover plate hingedly connected to said base plate, said cover plate having an open position allowing a sample to be introduced into said well and a closed position wherein a bottom surface of a section of said cover plate covers said well,
   wherein at least a portion of one of said section of said cover plate and said section of said base plate is reflective, transparent or translucent, and at least a portion of the other of said section of said cover plate and said section of said base plate is transparent or translucent.

2. The sample tab of claim 1, wherein said wall extending above said top surface of said base plate comprises one, or more than one overflow opening, and is surrounded by a containment wall, and wherein said containment wall and said wall extending above said top surface of said base plate define an overflow channel therebetween.

3. The sample tab of claim 2, wherein said containment wall comprises a sealing member on its upper surface.

4. The sample tab of claim 3, wherein said sealing member is an O ring.

5. The sample tab of claim 3, wherein said sealing member is a pliable material integral with said containment wall.

6. The sample tab of claim 2, wherein said containment wall is circular.

7. The sample tab of claim 6, wherein said wall extending above said top surface of said base plate is circular.

8. The sample tab of claim 1, further comprising a locking member for locking said cover plate to said base plate when said cover plate is in said closed position.

9. The sample tab of claim 2, further comprising a locking member for locking said cover plate to said base plate when said cover plate is in said closed position.

10. The sample tab of claim 9, wherein said locking member comprises a circular ring for frictionally engaging an outer portion of said containment wall when said cover plate is in said closed position, wherein said locking member is disposed on said cover plate.

11. The sample tab of claim 9, wherein said containment wall comprises a sealing member on its upper surface.

12. The sample tab of claim 11, wherein said sealing member is an O ring.

13. The sample tab of claim 11, wherein said sealing member is a pliable material integral with said containment wall.

14. The sample tab of claim 9, wherein said locking member comprises one, or more than one clip for locking said cover plate to said base plate in said closed position.

15. The sample tab of claim 9, wherein said locking member is on said cover plate, said base plate or both said cover plate and said base plate.

16. The sample tab of claim 8, wherein said locking member comprises one, or more than one clip for locking said cover plate to said base plate in said closed position.

17. The sample tab of claim 8, wherein said locking member is on said cover plate, said base plate or both said cover plate and said base plate.

18. A method for sample analysis, comprising:
   (i) adding a sample into the well of said sample tab defined in claim 1,
   (ii) closing said cover plate of said sample tab,
   (iii) inserting said sample tab into an instrument for analyzing said sample, and
   (iv) analyzing said sample.

19. The method of claim 18, wherein said cover plate comprises a locking member for locking said cover plate to said base plate when said cover plate is in said closed position.

20. The method of claim 19, wherein said sample is either a biological or a non-biological sample.

21. The method of claim 20, wherein said sample is a semi-solid or a fluid sample.

22. The method of claim 18, wherein in said step of inserting (step iii), said sample tab is placed in a horizontal position within a sample holder of said instrument, and wherein said sample is analyzed by projecting electromagnetic radiation through said well in a direction substantially perpendicular to the position of said sample tab.

23. The sample tab of claim 1, wherein said wall extending above said top surface of said base plate is circular.

24. The sample tab of claim 1, wherein at least a portion of said section of said cover plate is transparent or translucent and at least a portion of said section of said base plate is transparent or translucent.

25. The sample tab of claim 1, wherein at least a portion of said section of said cover plate is transparent or translucent and at least a portion of said section of said base plate is reflective.

26. The sample tab of claim 1, wherein at least a portion of said section of said cover plate is reflective and at least a portion of said section of said base plate is transparent or translucent.

27. The sample tab of claim 1, wherein said section of said cover plate is transparent or translucent and said section of said base plate is transparent or translucent.

28. The sample tab of claim 1, wherein said section of said cover plate is transparent or translucent and said section of said base plate is reflective.

29. The sample tab of claim 1, wherein said section of said cover plate is reflective and said section of said base plate is transparent or translucent.

* * * * *